US006159178A

United States Patent [19]
Sharkawy et al.

[11] Patent Number: 6,159,178
[45] Date of Patent: *Dec. 12, 2000

[54] METHODS AND DEVICES FOR OCCLUDING THE ASCENDING AORTA AND MAINTAINING CIRCULATION OF OXYGENATED BLOOD IN THE PATIENT WHEN THE PATIENT'S HEART IS ARRESTED

[75] Inventors: A. Adam Sharkawy, Redwood City; Wesley D. Sterman, San Francisco; David M. Taylor, Fremont; Pinaki Ray, Hayward, all of Calif.

[73] Assignee: Heartport, Inc., Redwood City, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 09/012,833

[22] Filed: Jan. 23, 1998

[51] Int. Cl.[7] .................................................. A61M 29/00
[52] U.S. Cl. .................................. 604/103.08; 604/96.01
[58] Field of Search .............................. 604/916, 96, 101, 604/104, 96.01, 103.06, 103.08, 4.01, 6.16; 606/192, 194

[56] References Cited

U.S. PATENT DOCUMENTS

| | | |
|---|---|---|
| Re. 33,258 | 7/1990 | Onik et al. . |
| 2,308,484 | 1/1943 | Auzin et al. . |
| 2,854,982 | 10/1958 | Pagano . |
| 3,385,300 | 5/1968 | Holter . |
| 3,635,223 | 1/1972 | Klieman . |
| 3,674,014 | 7/1972 | Tillander . |
| 3,692,018 | 9/1972 | Goetz et al. . |
| 3,766,924 | 10/1973 | Pidgeon . |
| 3,769,960 | 11/1973 | Robinson . |
| 3,788,328 | 1/1974 | Alley et al. . |
| 3,833,003 | 9/1974 | Taricco . |
| 3,837,347 | 9/1974 | Tower . |

(List continued on next page.)

FOREIGN PATENT DOCUMENTS

| | | |
|---|---|---|
| 0 161 045 | 11/1985 | European Pat. Off. . |
| 0 218 275 | 4/1987 | European Pat. Off. . |
| 0 238 106 | 9/1987 | European Pat. Off. . |
| 0 249 338 | 12/1987 | European Pat. Off. . |
| 0 277 367 | 8/1988 | European Pat. Off. . |
| 0 321 614 | 6/1989 | European Pat. Off. . |
| 0 335 205 | 10/1989 | European Pat. Off. . |
| 0 414 350 | 2/1991 | European Pat. Off. . |
| 2246526 | 3/1973 | Germany . |
| 334404 | 1/1936 | Italy . |
| 1271508 | 11/1986 | U.S.S.R. . |
| 1371701 | 2/1988 | U.S.S.R. . |
| 1097881 | 1/1968 | United Kingdom . |

(List continued on next page.)

OTHER PUBLICATIONS

Baxter Healthcare Corporation, "Fogarty Occlusion Catheter: Instructions for Use," ©1994.

Buckberg, G.D., "Strategies and Logic of Cardioplegic Delivery to Prevent, Avoid, and Reverse Ischemic and Reperfusion Damage," *J Thorac Vasc Surg*, 1987; 93:127–129.

Corday, et al., "Symposium on the Present Status of Reperfusion of the Acutely Ischemic Myocardium. Part I," *J. Am Coll Cardiol*, 1983; 1(4):1031–1036.

(List continued on next page.)

*Primary Examiner*—Sharon Kennedy
*Attorney, Agent, or Firm*—Jens E. Hoekendijk

[57] ABSTRACT

A method and device for occluding a patient's ascending aorta, maintaining circulation of oxygenated blood in the patient and delivering cardioplegic fluid to arrest the patient's heart. An aortic occlusion catheter has an occluding member for occluding the ascending aorta. The aortic occlusion catheter passes through a cannula. Delivery of oxygenated blood is accomplished through either the cannula or the aortic occlusion catheter.

11 Claims, 12 Drawing Sheets

6,159,178
Page 2

U.S. PATENT DOCUMENTS

| | | |
|---|---|---|
| 3,851,647 | 12/1974 | Monestere, Jr. et al. . |
| 3,889,686 | 6/1975 | Duturbure . |
| 3,903,895 | 9/1975 | Alley et al. . |
| 3,915,171 | 10/1975 | Shermeta . |
| 3,963,028 | 6/1976 | Cooley et al. . |
| 3,970,090 | 7/1976 | Loiacono . |
| 3,983,879 | 10/1976 | Todd . |
| 4,000,739 | 1/1977 | Stevens . |
| 4,019,515 | 4/1977 | Kornblum et al. . |
| 4,029,104 | 6/1977 | Kerber . |
| 4,073,297 | 2/1978 | Kopp . |
| 4,122,858 | 10/1978 | Schiff . |
| 4,154,227 | 5/1979 | Krause et al. . |
| 4,173,981 | 11/1979 | Mortensen . |
| 4,204,328 | 5/1980 | Kutner . |
| 4,248,224 | 2/1981 | Jones . |
| 4,276,874 | 7/1981 | Wolvek et al. . |
| 4,284,073 | 8/1981 | Krause et al. . |
| 4,285,341 | 8/1981 | Pollack . |
| 4,287,892 | 9/1981 | Schiff . |
| 4,289,129 | 9/1981 | Turner . |
| 4,290,428 | 9/1981 | Durand et al. . |
| 4,301,803 | 11/1981 | Handa et al. . |
| 4,304,239 | 12/1981 | Perlin . |
| 4,310,017 | 1/1982 | Raines . |
| 4,323,071 | 4/1982 | Simpson et al. . |
| 4,327,709 | 5/1982 | Hanson et al. . |
| 4,328,056 | 5/1982 | Snooks . |
| 4,351,341 | 9/1982 | Goldberg et al. . |
| 4,405,313 | 9/1983 | Sisley et al. . |
| 4,411,055 | 10/1983 | Simpson et al. . |
| 4,413,989 | 11/1983 | Schjeldahl et al. . |
| 4,417,576 | 11/1983 | Baran . |
| 4,430,081 | 2/1984 | Timmermans . |
| 4,439,186 | 3/1984 | Kuhl . |
| 4,441,495 | 4/1984 | Hicswa . |
| 4,451,251 | 5/1984 | Osterholm . |
| 4,456,000 | 6/1984 | Schjeldahl et al. . |
| 4,459,977 | 7/1984 | Pizon et al. . |
| 4,464,175 | 8/1984 | Altman et al. . |
| 4,493,697 | 1/1985 | Krause et al. . |
| 4,496,345 | 1/1985 | Hasson . |
| 4,497,325 | 2/1985 | Wedel . |
| 4,512,762 | 4/1985 | Spears . |
| 4,527,549 | 7/1985 | Gabbay . |
| 4,531,935 | 7/1985 | Berryessa . |
| 4,531,936 | 7/1985 | Gordon . |
| 4,535,757 | 8/1985 | Webster, Jr. . |
| 4,540,399 | 9/1985 | Litzie et al. . |
| 4,552,558 | 11/1985 | Muto . |
| 4,573,966 | 3/1986 | Weikl et al. . |
| 4,580,568 | 4/1986 | Gianturco . |
| 4,592,340 | 6/1986 | Boyles . |
| 4,596,552 | 6/1986 | DeVries . |
| 4,601,706 | 7/1986 | Aillon . |
| 4,601,713 | 7/1986 | Fuqua . |
| 4,610,661 | 9/1986 | Possis et al. . |
| 4,631,052 | 12/1986 | Kensey . |
| 4,639,252 | 1/1987 | Kelly et al. . |
| 4,648,384 | 3/1987 | Schmukler . |
| 4,664,125 | 5/1987 | Pinto . |
| 4,681,117 | 7/1987 | Brodman et al. . |
| 4,686,085 | 8/1987 | Osterholm . |
| 4,689,041 | 8/1987 | Corday et al. . |
| 4,692,148 | 9/1987 | Kantrowitz et al. . |
| 4,697,574 | 10/1987 | Karcher et al. . |
| 4,704,102 | 11/1987 | Guthery . |
| 4,705,507 | 11/1987 | Boyles . |
| 4,714,460 | 12/1987 | Calderon . |
| 4,721,109 | 1/1988 | Healey . |
| 4,722,347 | 2/1988 | Abrams et al. . |
| 4,722,732 | 2/1988 | Martin . |
| 4,723,550 | 2/1988 | Bales et al. . |
| 4,723,936 | 2/1988 | Buchbinder et al. . |
| 4,741,328 | 5/1988 | Gabbay . |
| 4,751,924 | 6/1988 | Hammerschmidt et al. . |
| 4,753,637 | 6/1988 | Horneffer . |
| 4,767,409 | 8/1988 | Brooks . |
| 4,770,652 | 9/1988 | Mahurkar . |
| 4,771,777 | 9/1988 | Horzewski et al. . |
| 4,777,951 | 10/1988 | Cribier et al. . |
| 4,785,795 | 11/1988 | Singh . |
| 4,787,899 | 11/1988 | Lazarus . |
| 4,787,901 | 11/1988 | Baykut . |
| 4,790,825 | 12/1988 | Bernstein et al. . |
| 4,794,928 | 1/1989 | Kletschka . |
| 4,796,629 | 1/1989 | Grayzel . |
| 4,798,588 | 1/1989 | Aillon . |
| 4,804,358 | 2/1989 | Karcher et al. . |
| 4,804,365 | 2/1989 | Litzie et al. . |
| 4,808,165 | 2/1989 | Carr . |
| 4,809,681 | 3/1989 | Kantrowitz et al. . |
| 4,811,737 | 3/1989 | Rydell . |
| 4,821,722 | 4/1989 | Miller et al. . |
| 4,830,849 | 5/1989 | Osterholm . |
| 4,848,344 | 7/1989 | Sos et al. . |
| 4,850,969 | 7/1989 | Jackson . |
| 4,865,581 | 9/1989 | Lundquist et al. . |
| 4,877,031 | 10/1989 | Conway et al. . |
| 4,877,035 | 10/1989 | Bogen et al. . |
| 4,878,495 | 11/1989 | Grayzel . |
| 4,883,458 | 11/1989 | Shiber . |
| 4,886,507 | 12/1989 | Patton et al. . |
| 4,889,137 | 12/1989 | Kolobow . |
| 4,898,168 | 2/1990 | Yule . |
| 4,902,272 | 2/1990 | Milder et al. . |
| 4,902,273 | 2/1990 | Choy et al. . |
| 4,911,163 | 3/1990 | Fina . |
| 4,917,667 | 4/1990 | Jackson . |
| 4,923,450 | 5/1990 | Maeda et al. . |
| 4,927,412 | 5/1990 | Menasche . |
| 4,934,996 | 6/1990 | Mohl et al. . |
| 4,943,275 | 7/1990 | Stricker . |
| 4,943,277 | 7/1990 | Bolling . |
| 4,960,412 | 10/1990 | Fink . |
| 4,966,604 | 10/1990 | Reiss . |
| 4,969,470 | 11/1990 | Mohl et al. . |
| 4,979,939 | 12/1990 | Shiber . |
| 4,985,014 | 1/1991 | Orejola . |
| 4,986,830 | 1/1991 | Owens et al. . |
| 4,990,143 | 2/1991 | Sheridan . |
| 4,994,032 | 2/1991 | Sugiyama et al. . |
| 4,994,033 | 2/1991 | Shockey et al. . |
| 5,007,896 | 4/1991 | Shiber . |
| 5,009,636 | 4/1991 | Wortley et al. . |
| 5,011,468 | 4/1991 | Lundquist et al. . |
| 5,011,469 | 4/1991 | Buckberg et al. . |
| 5,011,488 | 4/1991 | Ginsburg . |
| 5,013,296 | 5/1991 | Buckberg et al. . |
| 5,021,044 | 6/1991 | Sharkaway . |
| 5,021,045 | 6/1991 | Buckberg et al. . |
| 5,024,668 | 6/1991 | Peters et al. . |
| 5,026,366 | 6/1991 | Leckrone . |
| 5,033,998 | 7/1991 | Corday et al. . |
| 5,041,093 | 8/1991 | Chu . |
| 5,041,098 | 8/1991 | Loiterman et al. . |
| 5,047,041 | 9/1991 | Samuels . |
| 5,049,132 | 9/1991 | Shaffer et al. . |
| 5,053,008 | 10/1991 | Bajaj . |
| 5,059,167 | 10/1991 | Lundquist et al. . |
| 5,069,661 | 12/1991 | Trudell . |
| 5,069,662 | 12/1991 | Bodden . |

| | | |
|---|---|---|
| 5,073,168 | 12/1991 | Danforth . |
| 5,088,984 | 2/1992 | Fields . |
| 5,089,015 | 2/1992 | Ross . |
| 5,090,960 | 2/1992 | Don Michael . |
| 5,106,368 | 4/1992 | Uldall et al. . |
| 5,109,859 | 5/1992 | Jenkins . |
| 5,112,305 | 5/1992 | Barath et al. . |
| 5,116,305 | 5/1992 | Milder et al. . |
| 5,125,903 | 6/1992 | McLaughlin et al. . |
| 5,152,771 | 10/1992 | Sabbaghian et al. . |
| 5,167,628 | 12/1992 | Boyles . |
| 5,171,232 | 12/1992 | Castillo et al. . |
| 5,176,619 | 1/1993 | Segalowitz . |
| 5,181,518 | 1/1993 | McDonagh . |
| 5,186,713 | 2/1993 | Raible . |
| 5,195,942 | 3/1993 | Weil et al. . |
| 5,197,952 | 3/1993 | Marcadis et al. . |
| 5,216,032 | 6/1993 | Manning . |
| 5,219,326 | 6/1993 | Hattler . |
| 5,226,427 | 7/1993 | Buckberg et al. . |
| 5,236,413 | 8/1993 | Feiring . |
| 5,246,007 | 9/1993 | Frisbie et al. . |
| 5,250,038 | 10/1993 | Melker et al. . |
| 5,250,069 | 10/1993 | Nobuyoshi et al. . |
| 5,254,089 | 10/1993 | Wang . |
| 5,254,097 | 10/1993 | Schock et al. . |
| 5,270,005 | 12/1993 | Raible . |
| 5,275,622 | 1/1994 | Lazarus et al. . |
| 5,290,231 | 3/1994 | Marcadis et al. . |
| 5,295,958 | 3/1994 | Shturman . |
| 5,308,320 | 5/1994 | Safar et al. . |
| 5,312,344 | 5/1994 | Grinfeld et al. . |
| 5,314,418 | 5/1994 | Takano et al. . |
| 5,322,500 | 6/1994 | Rickerd . |
| 5,322,509 | 6/1994 | Johnson et al. . |
| 5,324,260 | 6/1994 | O'Neill et al. . |
| 5,330,451 | 7/1994 | Gabbay . |
| 5,334,142 | 8/1994 | Paradis . |
| 5,370,618 | 12/1994 | Leonhardt . |
| 5,370,640 | 12/1994 | Kolff . |
| 5,374,245 | 12/1994 | Mahurkar . |
| 5,380,282 | 1/1995 | Burns . |
| 5,382,239 | 1/1995 | Orr et al. . |
| 5,383,854 | 1/1995 | Safar et al. . |
| 5,383,856 | 1/1995 | Bersin ..................................... 604/101 |
| 5,385,548 | 1/1995 | Williams et al. ........................ 604/96 |
| 5,395,330 | 3/1995 | Marcadis et al. . |
| 5,395,331 | 3/1995 | O'Neill et al. . |
| 5,397,306 | 3/1995 | Nobuyoshi et al. . |
| 5,411,027 | 5/1995 | Wiklund et al. . |
| 5,411,479 | 5/1995 | Bodden . |
| 5,411,552 | 5/1995 | Andersen et al. . |
| 5,421,825 | 6/1995 | Farcot . |
| 5,425,708 | 6/1995 | Nasu . |
| 5,428,070 | 6/1995 | Cooke et al. . |
| 5,433,700 | 7/1995 | Peters . |
| 5,437,633 | 8/1995 | Manning . |
| 5,439,443 | 8/1995 | Miyata et al. . |
| 5,443,446 | 8/1995 | Shturman . |
| 5,451,207 | 9/1995 | Yock . |
| 5,456,665 | 10/1995 | Postell et al. . |
| 5,458,574 | 10/1995 | Machold et al. . |
| 5,478,309 | 12/1995 | Sweezer et al. . |
| 5,487,730 | 1/1996 | Marcadis et al. . |
| 5,499,996 | 3/1996 | Hill . |
| 5,505,698 | 4/1996 | Booth et al. . |
| 5,509,897 | 4/1996 | Twardowski et al. . |
| 5,525,388 | 6/1996 | Wand et al. . |
| 5,527,292 | 6/1996 | Adams et al. . |
| 5,533,957 | 7/1996 | Aldea . |
| 5,562,606 | 10/1996 | Huybregts . |
| 5,578,010 | 11/1996 | Ashby . |
| 5,584,803 | 12/1996 | Stevens et al. . |
| 5,591,129 | 1/1997 | Shoup et al. . |
| 5,595,181 | 1/1997 | Hubbard . |
| 5,597,377 | 1/1997 | Aldea . |
| 5,599,329 | 2/1997 | Gabbay . |
| 5,662,607 | 9/1997 | Booth et al. ............................. 604/104 |
| 5,749,852 | 5/1998 | Schwab et al. ........................ 604/96 |
| 5,765,568 | 6/1998 | Sweezer, Jr. et al. ................... 604/96 |
| 5,827,237 | 10/1998 | Macoviak et al. ....................... 604/96 |
| 6,048,332 | 4/2000 | Duffy et al. ............................ 604/96 |

FOREIGN PATENT DOCUMENTS

| | | |
|---|---|---|
| 1097882 | 1/1968 | United Kingdom . |
| 1284701 | 8/1972 | United Kingdom . |
| 1414344 | 11/1975 | United Kingdom . |
| 1467976 | 3/1977 | United Kingdom . |
| 1477665 | 6/1977 | United Kingdom . |
| 1513918 | 6/1978 | United Kingdom . |
| WO 91/03613 | 12/1981 | WIPO . |
| WO 83/03204 | 9/1983 | WIPO . |
| WO 89/10155 | 11/1989 | WIPO . |
| WO 91/01689 | 2/1991 | WIPO . |
| WO 91/08791 | 6/1991 | WIPO . |
| WO 91/10456 | 7/1991 | WIPO . |
| WO 91/17720 | 11/1991 | WIPO . |
| WO 92/17118 | 10/1992 | WIPO . |
| WO 93/07927 | 4/1993 | WIPO . |
| WO 95/30447 | 11/1995 | WIPO . |

OTHER PUBLICATIONS

Cosgrove, "Management of the Calcified Aorta: An Alternative Method of Occlusion," *Ann Thorac Surg*, 1983;36:718–719.

Crooke, et al., "Biventricular Distribution of Cold Blood Cardioplegic Solution Administered by Different Retrograde Techniques," *J Cardiac Thorac Surg*, 1991;102(4):631–636.

Datascope FDA 510(k) Application, "PERCLUDER–DL Occluding Balloon," Oct. 12, 1993.

DLP, Inc., Directions for Use: Cardioplegic Pressure Cannula with Vent Line, Code #24009 9 Gauge (no date).

DLP Medtronic Alternative Access Cannulae Brochure, ©1995.

DLP Worldwide Medical Innovations, Instrument Listings, pp. 5–9.

Douville, et al., "Retrograde Versus Antegrade Cardioplegia: Impact on Right Ventricular Function," *Ann Thorac Surg*, 1992: 54:56–61.

Drinkwater, et al., "The Use of Combined Antegrade–Retrograde Infusion of Blood Cardioplegic Solution in Pediatric Patients Undergoing Heart Operations," *Thorac and Cardiovascular Surg*, 1992; 104(5):1349–1355.

Elecath, "Baim Coronary Sinus Flow Catheter for Jugular or Subclavian Entry," Catalog No. 75–2337, 1994.

Erath and Stoney, "Balloon Catheter Occlusion of the Ascending Aorta," *Ann Thorac Surg*, 1983;35:560–561.

Farcot, et al., "New Catheter–Pump System for Diastolic Synchronized Coronary Sinus Retroperfusion (D.S.R.)," *Med Prog Technol*, 1980; 8(1):29–37.

Farcot, et al., "Synchronized Retroperfusion of Coronary Veins for Circulatory Support of Jeopardized Ischemic Myocardium," *Am J Cardiol*, 1978; 41:1101–1201.

Foster and Threlkel, "Proximal Control of Aorta with a Balloon Catheter," *Surg Gynecology & Obstetrics*, 1971, pp. 693–694.

Gundry, et al., "A Comparison of Retrograde of Cardioplegia Versus Antegrade Cardioplegia in the Presence of Coronary Artery Obstruction," *Ann Thorac Surg*, 1984; 38(2):124–127.

Gundry, "Modification of Myocardial Ischemic in Normal and Hypertrophied Hearts Utilizing Diastolic Retroperfusion of the Coronary Veins," *J Thorac Cardiovasc Surg*, 1982; 83:659–669.

Haendchen, et al., "Prevention of Ischemic Injury and Early Reperfusion Derangements by Hypothermic Retroperfusion," *J Am Coll Cardiol*, 1983; 1(4):1067–1080.

Hammond, et al., "Retrograde Coronary Sinus Perfusion: A Method of Myocardial Protection in the Dog During Left Coronary Artery Occlusion," *Ann Surg*, 1967; 166(1):139–147.

Ishizaka, "Myocardial Protection by Retrograde Cardiac Perfusion with Cold Modified Krebs Solution through Coronary Sinus During Complete Ischemic Arrest for 120 Minutes," *J Jpn Assn Thorac Surg*, 1977;25(12);:1592–1601.

Kalmbach, et al., "Cardioplegia Delivery by Combined Aortic Root and Coronary Sinus Perfusion," *Ann Thorac Surg*, 1989; 47:316–317.

Kar and Nordlander, "Coronary Veins: An Alternate Route to Ischemic Myocardium," *Heart and Lung*, Mar. 1992, vol. 21, No. 2, pp. 148–155.

Leggett, et al., "Fiberoptic Cardioscopy Under Cardiopulmonary Bypass: Potential for Cardioscopy Surgery?" *Ann Thorac Surg*, 1994;58:222–225.

Lust, et al., "Improved Protection of Chronically Inflow-limited Myocardium with Retrograde Coronary Sinus Cardioplegia," *Circulation III*, 1988;78(5):217–223.

Markov, et al., "Reversal of Acute Myocardial Ischemia in Closed Chest Animals by Retrograde Perfusion of the Coronary Sinus with Arterial Blood," *Acta Cardiologica*, 1976; XXXI(3):185–199.

Medex, Inc. Product Brochure, Angioplasty Kits and Accessories and PTCA Valve, 1990.

Medex, Inc., MX220 Single Tuohy–Borst Adaptor: Instructions for Use, 1992.

Medi–Tech, Boston Scientific Corporation, "Occlusion Balloon Catheters: Instructions for Use," Rev. Jun., 1991.

Medtronic Bio–Medicus, Inc., "Bio–Medicus Cannula Instructions for Use Manual, Sterile and Non–Pyrogenic Single–Use Only," PN 85281 Rev C(10–91).

Medtronic Bio–Medicus, Inc., "Bio–Medicus Cannula Introducer Instructions for Use Manual," PN 85146–Rev. C(Jul. 1991).

Medtronic Bio–Medicus Femoral Cannulae advertisement, ©1991.

Medtronic Bio–Medicus Pediatric Cannulae advertisement, ©1991.

Medtronic Bio–Medicus Percutaneous Cannula Kits advertisements, ©1991.

Meerbaum, et al., "Diastolic Retroperfusion of Acutely Ischemic Myocardium," *Am J Cardiol*, 1976; 37:588–598.

Meerbaum, et al., "Hypothermic Coronary Venous Phased Retroperfusion: A Closed–Chest Treatment of Acute Regional Myocardial Ischemia," *Circulation*, 1982; 65(7): 1435–1445.

Meerbaum, et al., "Retrograde Lysis of Coronary Artery Thrombus by Coronary Venouse Strepokinase Administration," *J Am Coll Cardiol*, 1983; 1(5):1262–1267.

Menasche, et al., Cardioplegia by Way of the coronary Sinus for Valvular and Coronary Surgery, *JACC*, 1991; 18(2):628–636.

Menasche, et al., "Retrograde Cardioplegia through the Coronary Sinus," *Ann Thorac Surg*, 1987; 44:214–216.

Menasche, et al., "Retrograde Coronary Sinus Cardioplegia for Aortic Valve Operations: A Clinical Report on 500 Patients," *Ann Thorac Surg*, 1990; 49:556–564.

Menasche, et al., "Retrograde Warm Blood Cardioplegia Preserves Hypertrophied Myocardium: A Clinical Study," *Ann Thorac Surg*, 1994; 57:1429–1435.

"Valvular Heart Disease," Merck Manual of Diagnosis and Therapy, sixteenth ed, 1992, pp. 546–553.

Ogawa, K. "Aortic Arch Reconstruction Without Aortic Cross–Clamping Using Separate Extracorporeal Circulation," *J Jpn Assn Thorac Surg*, 1993; pp. 2185–2190.

Okita, et al., "Utilization of Triple–Lumen Balloon Catheter for Occlusion of the Ascending Aorta During Distal Aortic Arch Surgery with Hypothermic Retrograde Cerebral Circulation Technique Through Left Thoracotomy," *Journal of Cardiac Surgery*, 1996; 10:699–702.

Peters, W. S., "The Promise of Cardioscopic Surgery," *AustralAs J Cardiac Thorac Surg*, 1993; 2(3):152–154.

Pilling Surgical Instruments, Vascular Clamps—Cooley Brochure, p. 385 (no date).

Razi, D..M., "The Challenge of Calcific Aortitis," *J Cardiac Surg*, 1993; 8:102–107.

Research Medical, Inc., Cardioplegia Products, Product Catalog 1995.

Research Medical, Inc., Fem Flex Femoral Percutaneous Cannulae, advertisement, *Ann Thorac Surg*, Jan., 1995, p. A38.

Ropchan, et al., "Salvage of Ischemic Myocardium by Nonsynchronized Retroperfusion in the Pig," *The Journal of Thoracic and Cardiovascular Surgery*, Sep. 1992, vol. 104, No. 3, pp. 619–625.

Rossi, "Long–term Cardiopulmonary Bypass by Peripheral Cannulation in a Model of Total Heart Failure," *J Thorac Cardiac Vasc Surg*, 1990;100:914–921.

Sabiston, D.C., Textbook of Surgery, $10^{th}$ Ed., 1972, pp. 2021–2023, 2114–2121.

Sakaguchi et al, "Aortic Valve Replacement and Coronary Artery Bypass," *J Jpn Assoc for Thoracic Surg*, 1993;41(6):1063–1068.

Shumway, "Forward Versus Retrograde Coronary Perfusion for Direct Vision Surgery of Acquired Aortic Valvular Disease," *J Thoracic and Cardiovasc Surg*, 1959; 75–80.

Takahashi, M., "Retrograde Coronary Sinus Perfusion for Myocardial protection in Aortic A valve Surgery," *J Jpn Assn Thorac Surg*, 1982;30(3):306–318.

Uchida et al, "Percutaneous Cardiomyotomy ad Valvulotomy with Angioscopic Guidance," *American Heart Journal*, 1991;121(4, part I):1221–1224.

Uchida, et al., "Percutaneous Fiberoptic Angioscopy of the Cardiac Valves," *Am Heart J*, 1991;121(6, part I):1791–1798.

Yamaguchi, A., "A Case of Reoperation Using a Balloon Catheter with Blocked Pars Ascendes Aortae," *Kyobu Geka*, Oct. 1989; 42(11):961–964.

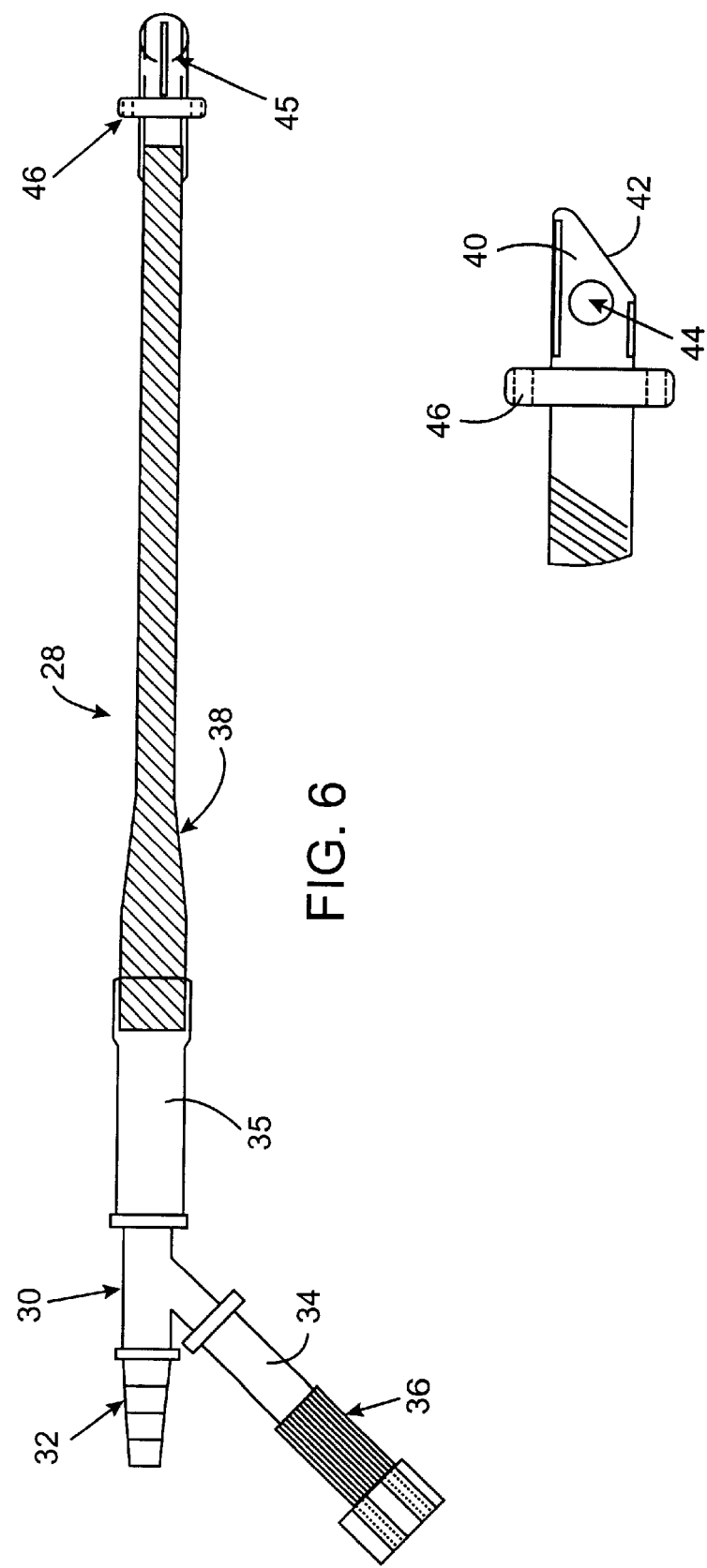

METHODS AND DEVICES FOR OCCLUDING THE ASCENDING AORTA AND MAINTAINING CIRCULATION OF OXYGENATED BLOOD IN THE PATIENT WHEN THE PATIENT'S HEART IS ARRESTED

BACKGROUND OF THE INVENTION

The present invention is directed to methods and devices for occluding a patient's ascending aorta and maintaining circulation of oxygenated blood in the patient when the patient's heart is arrested. Such devices and methods are useful for performing various procedures on a patient's vascular system and heart such as the procedures described in U.S. Pat. Nos. 5,584,803 and 5,682,906 which describe coronary artery bypass grafting (CABG) and valve procedures, respectively. Another device and method for occluding a patient's ascending aorta is described in Re. 35,352.

The methods and devices described in the above-mentioned patents use an internal occlusion device to occlude the ascending aorta rather than a conventional external cross-clamp. Use of an internal occlusion device may reduce strokes as compared to conventional external cross-clamps since external cross-clamps distort and compress the aorta which may release emboli leading to strokes.

It is an object of the invention to provide alternative methods and devices for occluding a patient's ascending aorta and maintaining circulation of oxygenated blood when the patient's heart is arrested.

SUMMARY OF THE INVENTION

In accordance with the object of the invention, the present invention provides alternative methods and devices for occluding a patient's ascending aorta and maintaining circulation of oxygenated blood in a patient when the patient's heart is arrested.

In a first preferred method and device of the present invention, an aortic occlusion device having a blood delivery lumen and an occluding member is introduced into the patient's aortic arch. The occluding member has an interior in fluid communication with the blood delivery lumen so that delivery of oxygenated blood inflates the occluding member. An advantage of this method is that a separate inflation lumen is not necessary. The aortic occlusion device preferably passes through a cannula having a y-arm with the aortic occlusion catheter passing through an arm of the y-arm. The other arm of the y-arm connector is coupled to the source of oxygenated blood so that bypass support can be maintained even when the aortic occlusion device has been removed.

In another preferred method and device, oxygenated blood is delivered to the patient through the aortic occlusion catheter. The aortic occlusion catheter also passes through a cannula with a y-arm connector so that bypass support can be maintained when the aortic occlusion device is removed. The aortic occlusion device also preferably includes a lumen for delivering cardioplegic fluid and venting the ascending aorta and a pressure lumen for measuring pressure in the ascending aorta. If the lumens are not provided in the aortic occlusion device, delivery of cardioplegic fluid, venting of the ascending aorta and pressure monitoring may be accomplished with the cannula.

In another preferred device, the aortic occlusion device has an occluding member mounted to a side of the catheter. The occluding member has a pathway therethrough which is in communication with a lumen in the aortic occlusion catheter. The pathway directs cardioplegic fluid toward the coronary ostia while the aortic occlusion device directs the oxygenated blood in the direction of normal blood flow in the aorta.

These and other aspects and advantages of the present invention will become apparent from the following description and drawings.

BRIEF DESCRIPTION OF THE DRAWINGS

FIG. 6 shows a cannula;

FIG. 7 shows an enlarged view of the distal end of the cannula of FIG. 6;

DESCRIPTION OF THE PREFERRED EMBODIMENTS

Figure 1:
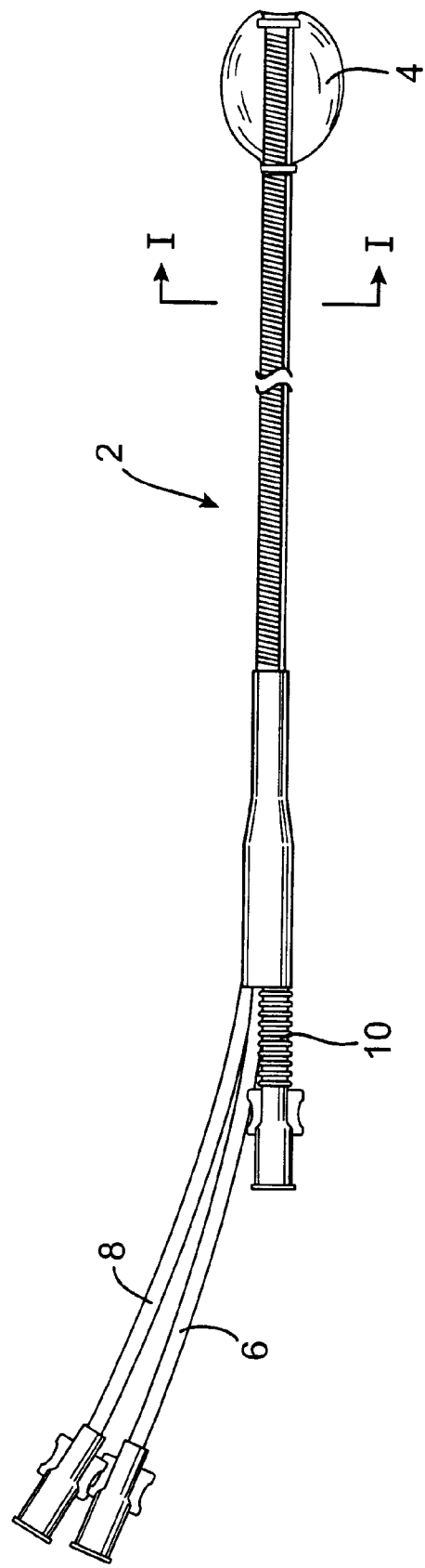
FIG. 1 shows an aortic occlusion device.
Figure 5:
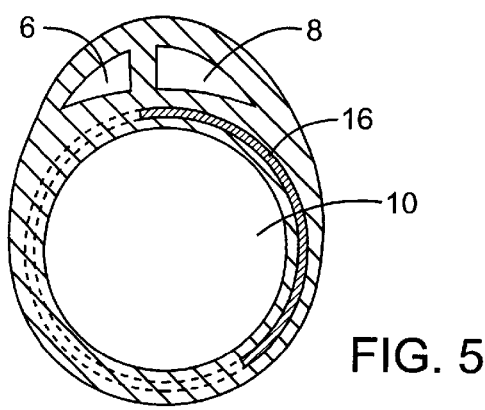
FIG. 5 is a cross-sectional view of FIG. 1 along line I-I.

Referring to FIGS. 1 and 5, an aortic occlusion device 2 is shown. The aortic occlusion device 2 has an occluding member 4 configured to occlude a patient's ascending aorta. The occluding member 4 is preferably a balloon but may also be a mechanically actuated member. The aortic occlusion device 2 has an inflation lumen 6 for inflating the occluding member 4, a pressure lumen 8 for measuring pressure in the ascending aorta, and a lumen 10 for delivering cardioplegic fluid and/or venting the ascending aorta. The aortic occlusion device 2 is preferably manufactured and used in the manner described in U.S. patent application Ser. No. 08/782,113 but may also be manufactured in any other manner such as an extrusion.

The aortic occlusion device 2 is preferably substantially straight in an unbiased position, however, the aortic occlusion device 2 may also have a shaped end. For example, the aortic occlusion catheter 2 can have an L-shaped end which facilitates positioning the occluding member 4 in the ascending aorta depending upon the surgical approach. The aortic occlusion device 2 is preferably flexible so that it can be bent as necessary without kinking.

Figure 2:
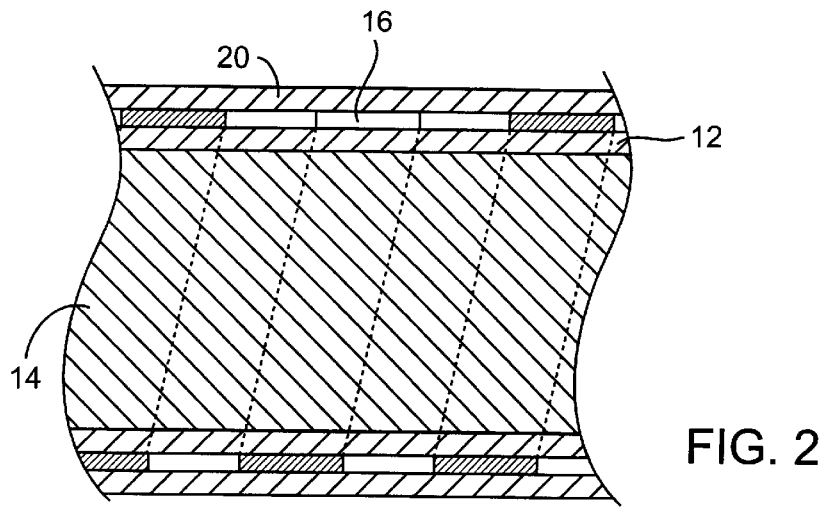
FIG. 2 is a cross-sectional view of a first step in forming the aortic occlusion catheter of FIG. 1.
Figure 3:
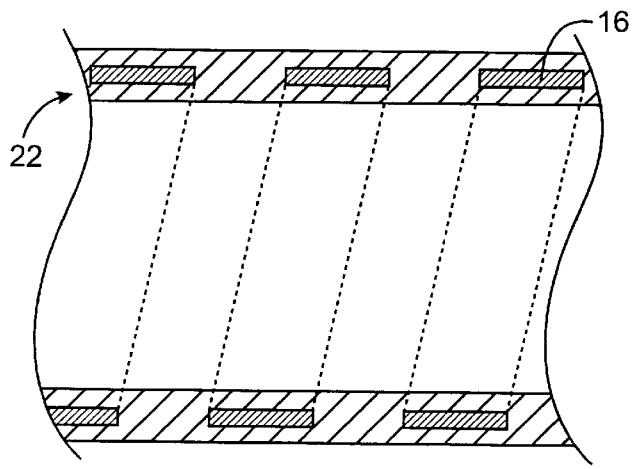
FIG. 3 is a cross-sectional view of the structure of FIG. 2 after heating.

Referring to FIGS. 2–5, a preferred method of forming the aortic occlusion device 2 is shown. FIG. 2 shows a longitudinal cross-section of a tube 12, preferably a urethane tube, mounted on a teflon-coated mandrel 14 with the elongate element 16 wound helically around the tube 12. The elongate element 16 is preferably a wire ribbon having a thickness of 0.003 inch and a width of 0.012 inch. The elongate element 16 is preferably wrapped around the tube 12 with a spacing of 0.010 inch. Another tube 20 is positioned over the elongate member 16 and a shrink tube (not shown) is positioned over the tube 20. The entire structure is then heated to fuse the tubes together to form a reinforced tube 22 which is shown in longitudinal crosssection in FIG. 3. The resulting reinforced tube 22 preferably has an inner diameter of about 0.100 inch and a wall thickness of about 0.010 inch.

Figure 4:
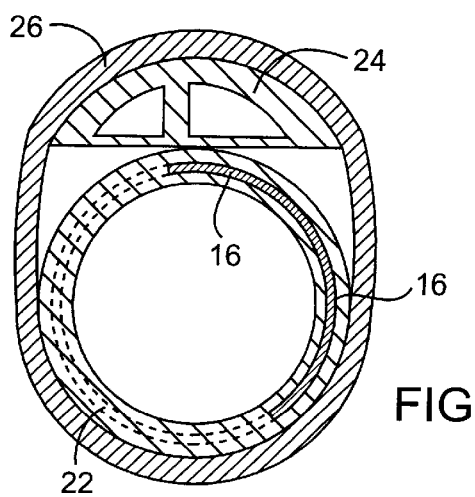
FIG. 4 is a cross-sectional view of a further step in forming the aortic occlusion catheter of FIG. 1.

Referring to FIG. 4, a two-lumen member 24 is positioned against the reinforced tube 22 and a shrink tube 26 is positioned around the member 24 and reinforced tube 22. The two-lumen member 24 has the inflation lumen 6, which is used for inflating the occluding member 4, and the pressure lumen 8, which is used for pressure monitoring in the ascending aorta. The two-lumen member 24 is preferably an extrusion having a D-shaped outer surface in cross-section. The member 24 and tube 22 aire then heated and the shrink tube 26 is removed to obtain the egg-shaped cross-sectional shape shown in FIG. 5. The cross-sectional shape is preferably about 0.145 inch tall and 0.125 inch wide. The inflation lumen 6 is then pierced to provide an inflation path to the occluding member 4 and the occluding member 4 is then mounted to the shaft.

Referring to FIGS. 6 and 7, a cannula 28 is shown which is used to return oxygenated blood to the patient when the patient's heart is arrested. The aortic occlusion device 2 is introduced into the patient through the cannula 28 as will be described below. The cannula 28 has a y-arm connector 30 with first and second arms 32, 34 with each coupled to a lumen 35. The second arm 34 has a hemostasis valve 36 which may be any hemostasis valve and is preferably a Thouy-Borst valve. The cannula 28 has a reinforced body 38 which is preferably formed in the manner described in U.S. Pat. No. 5,863,366, which is hereby incorporated by reference, however, any other method may be used including extrusion. The distal end 40 of the cannula 28 is beveled and has an open end 42 and two side ports 44 for infusing oxygenated blood into the patient. A radiopaque markers 45 are provided at the distal end for visualization as discussed below.

Figure 9:
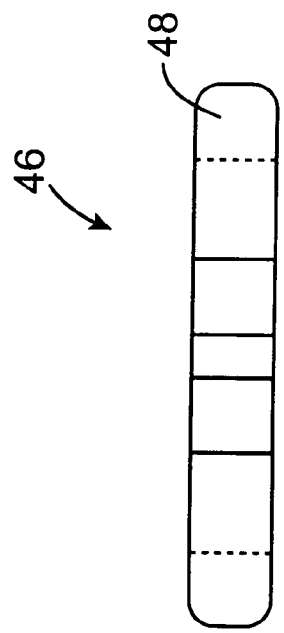
FIG. 9 is a side view of the ring.
Figure 8:
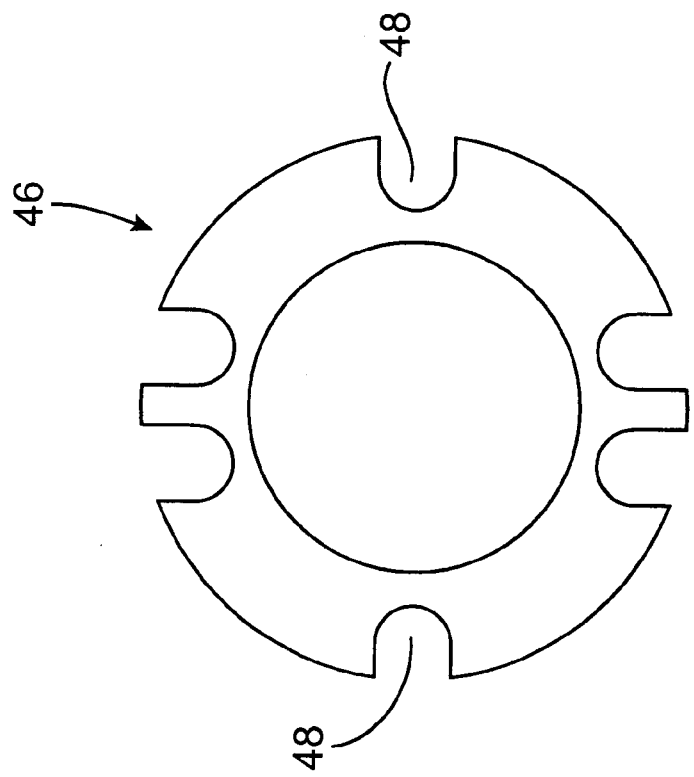
FIG. 8 is a plan view of a ring.

Referring to FIGS. 6–9, a ring 46 is attached to the distal end 40 of the cannula 28. The ring 46 limits insertion of the cannula 28 into the vessel, stabilizes the cannula 28, and receives purse-string sutures which provide hemostasis around the cannula 28 when the cannula 28 is positioned in a vessel. Referring to FIGS. 8 and 9, the ring 46 has slots 48 which may receive purse-string sutures as will be described below.

Figure 10:
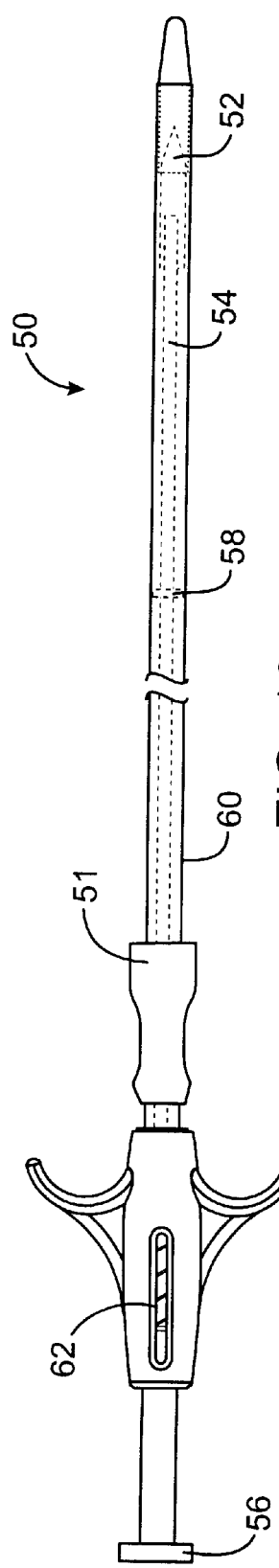
FIG. 10 shows an introducer with an incising element in a retracted position.
Figure 11:
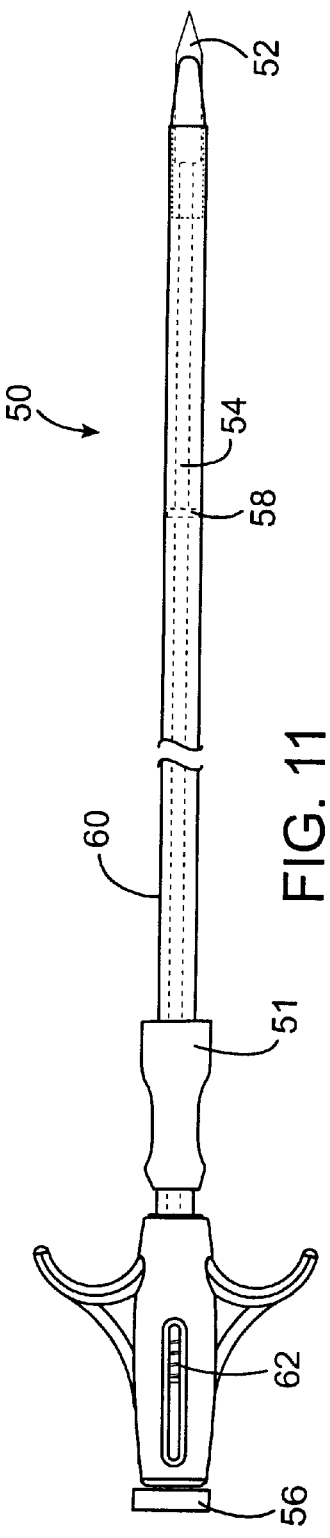
FIG. 11 shows the introducer with the incising element in an exposed position.

Referring to FIGS. 10 and 11, an introducer 50 is positioned in the cannula 28 to introduce the cannula 28 into a vessel. The introducer 50 has a connector hub 51 which is received by the hemostasis valve 36 on the second arm 32 of the cannula 28 to seal the space between the introducer 50 and cannula 28. The introducer 50 has an incising element 52 for incising the vessel into which the cannula 28 is introduced. The incising element 52 is attached to a shaft 54 which is coupled to a trigger 56 for moving the incising element 52 from the retracted position of FIG. 10 to the exposed position of FIG. 11. An o-ring seals 58 the space between an outer housing 60 and the shaft 54. The incising element 52 is biased toward the retracted position by a spring 62 so that the incising element 52 is only exposed when the trigger 56 is actuated. When introducing the cannula 28 into the vessel, the trigger 56 is actuated to move the incising element 52 to the exposed position, the vessel is incised with the incising element 52 and the cannula 28 is inserted through the incision. As will be described below. one or more purse-string sutures are then used to form a hemostatic seal around the cannula 28. The incising element 52 may be omitted if a separate incising device is used.

Figure 12:
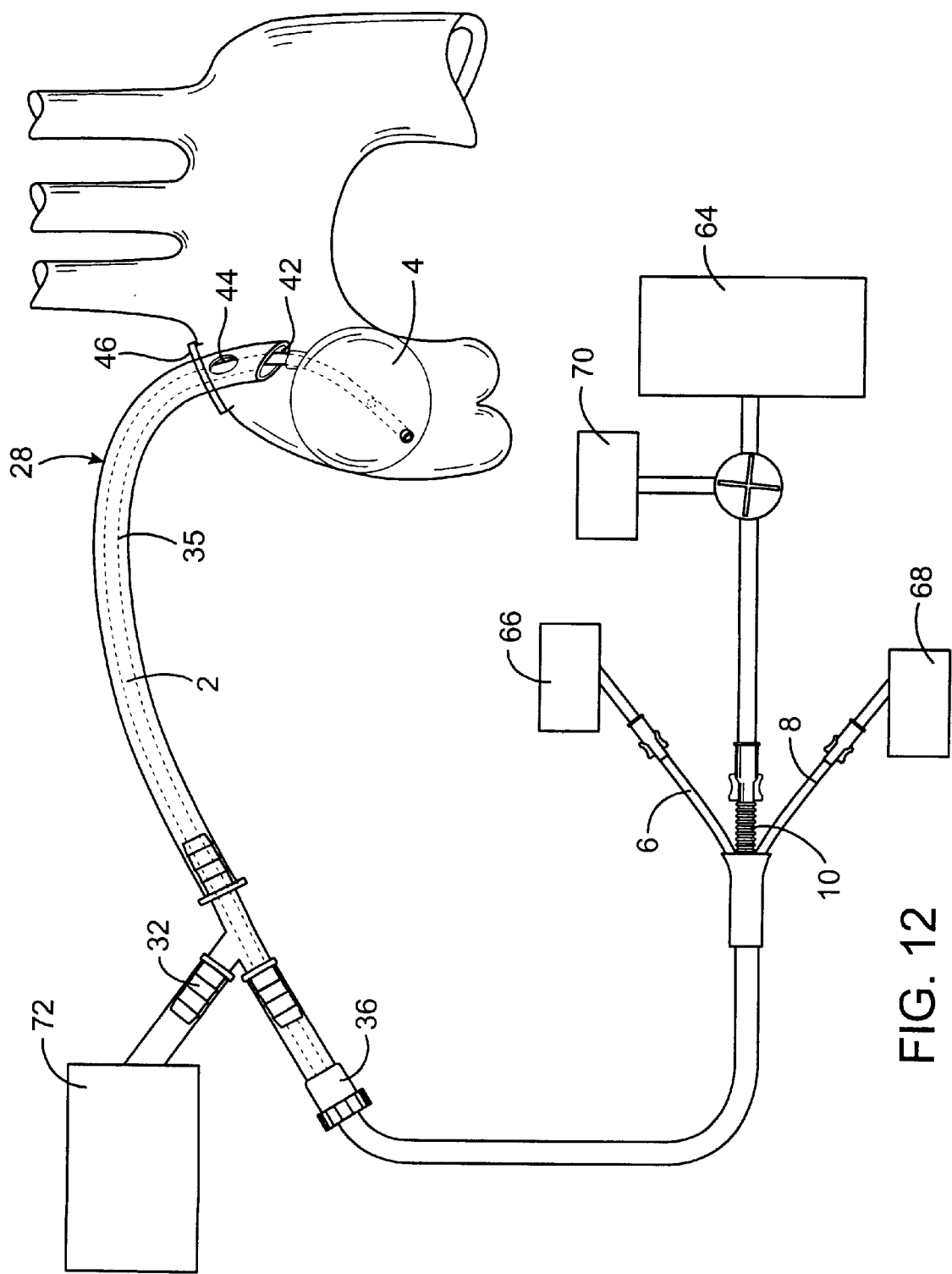
FIG. 12 shows the aortic occlusion device and cannula passing through a penetration in the ascending aorta.

Referring to FIGS. 12, the cannula 28 is positioned in a patient's ascending aorta with the aortic occlusion device 2 passing through the hemostasis valve 36. Placement of the cannula 28 and aortic occlusion device 2 into the position of FIG. 12 is described below. Referring to FIGS. 5 and 12, the lumen 10 is coupled to a source of cardioplegic fluid 64, the inflation lumen 6 is coupled to a source of inflation fluid 66, and the pressure lumen 8 is coupled to the pressure monitor 68 for measuring pressure in the ascending aorta. The lumen 10 is also coupled to a vacuum source 70 for venting the ascending aorta.

The first arm 32 of the cannula 28 is coupled to a source of oxygenated blood 72 so that blood is delivered through the lumen 35 of the cannula 28 with the blood passing through the annular area between the cannula 28 and the aortic occlusion device 2. The oxygenated blood passing through the open end 42 of the cannula 28 is directed at the occluding member 4 so that the oxygenated blood is not directed at the wall of the aorta. An advantage of directing the oxygenated blood at the occluding member 4 is that the fluid is dispersed radially outward by the occluding member 4 before coming into contact with the wall of the aorta. By directing the blood at the occluding member 4, rather than at the wall of the aorta, the likelihood of releasing emboli from the wall of the aorta may be reduced. Oxygenated blood is also directed through the side ports 44 so that oxygenated blood is delivered to the patient even if the occluding member 4 blocks the open end 42 of the cannula 28.

Figure 13:
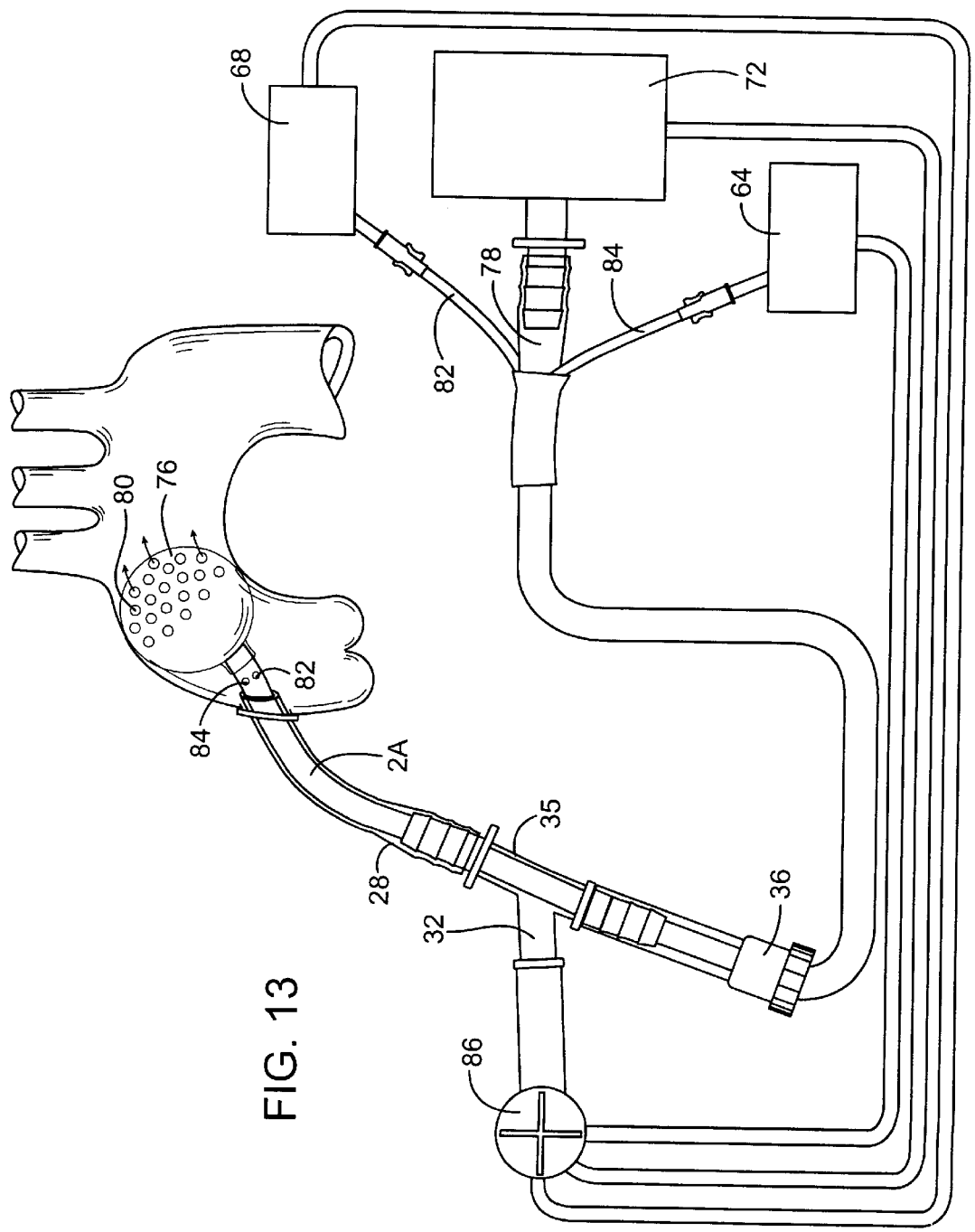
FIG. 13 shows another aortic occlusion device passing through the cannula and into the patient's ascending aorta.

Referring to FIG. 13, another aortic occlusion device 2A is shown having a balloon 76 which is inflated with the oxygenated blood delivered to the patient. The aortic occlusion device 2A has a blood flow lumen 78 which is fluidly coupled to the interior of the balloon 76 for inflating the balloon 76. Oxygenated blood is then delivered to the patient through an opening 80, preferably a number of openings, in the balloon 76. An advantage of the aortic occlusion device 2A is that a separate inflation lumen is not required since occlusion is accomplished by simply delivering oxygenated blood through the aortic occlusion device 2A. The aortic occlusion device 2A may also include a pressure lumen 82 for measuring pressure in the ascending aorta and a lumen 84 for delivering cardioplege and venting the ascending aorta. The aortic occlusion device 2A is preferably formed in the manner described above except that the lumen 78 is sized large enough to provide sufficient flow of oxygenated blood at an acceptable pressure. Acceptable blood flow rates and pressures are disclosed in the above-mentioned patents and patent applications which have been incorporated by reference. Although it is preferred to manufacture the device in the manner described above, the aortic occlusion device 2A may also simply be an extrusion or laminated structure. The balloon 76 is preferably made of silicone having a thickness of between 0.005 and 0.009 inch.

The aortic occlusion catheter 2A passes through the cannula 28 so that oxygenated blood can be delivered to the patient when the aortic occlusion device 2A is removed. The cannula 28 is preferably the cannula 28 described above with the first arm 32 coupled to the source of oxygenated blood 72, pressure monitor 68, and source of cardioplegic fluid via valve 86. Thus, cardioplegic fluid and oxygenated blood can be directed through the lumen 35 in the cannula 28 if the lumen 84 is not provided in the aortic occlusion catheter 2A. The cannula 28 has the hemostasis valve 36 to seal the space between the cannula 28 and aortic occlusion device 2A.

Figure 14:
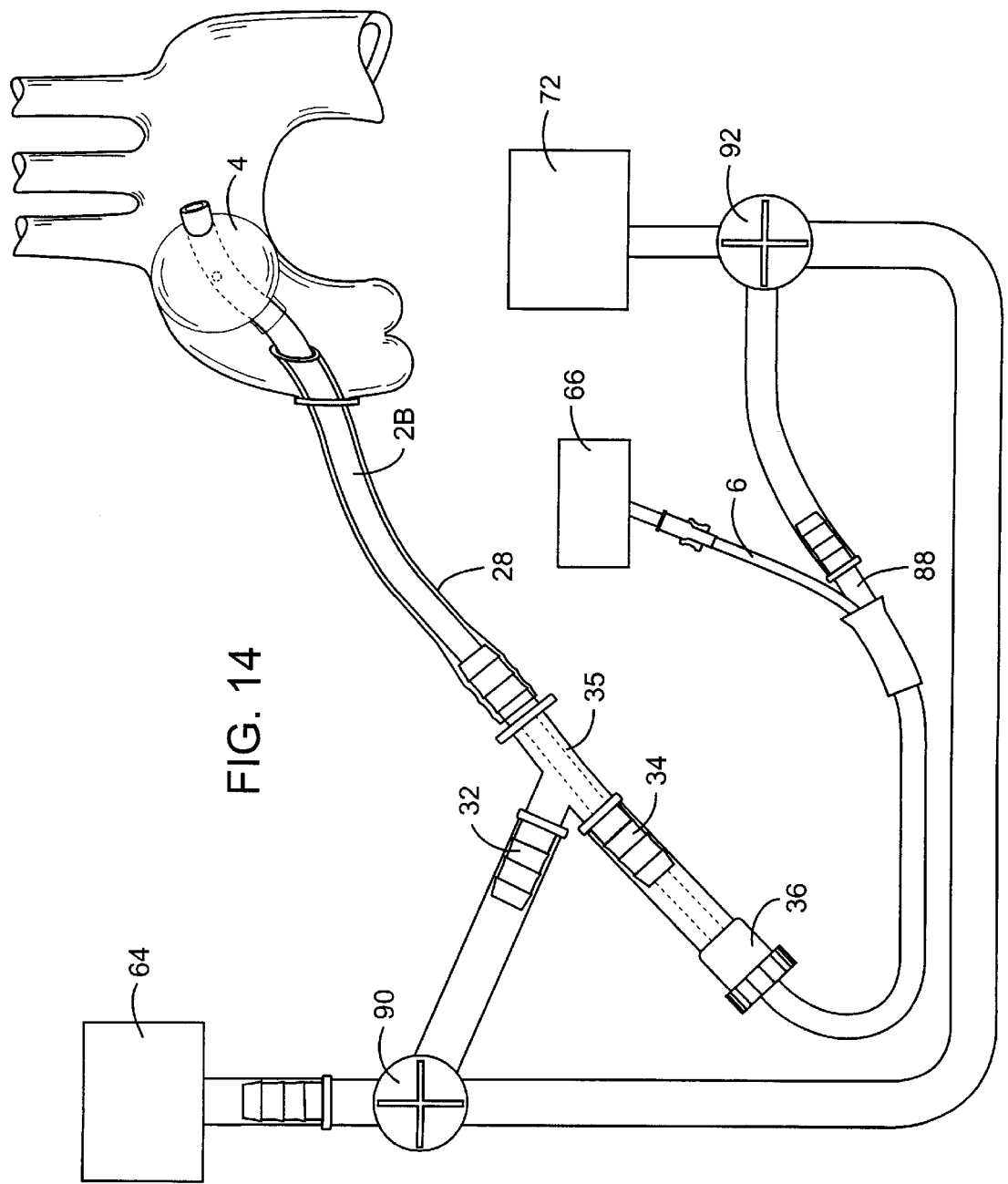
FIG. 14 shows yet another aortic occlusion device.

Referring to FIG. 14, yet another aortic occlusion device 2B is shown. The aortic occlusion device 2B has the occluding member 4 and the inflation lumen 6 coupled to the source of inflation fluid 66 for inflating the occluding member 4. The aortic occlusion device 2B also has a lumen 88 for delivering oxygenated blood to the patient from the source of oxygenated blood 64. The shaft is preferably reinforced with a wire in the manner described above except that the lumen 88 is sized large enough to provide adequate blood flow to the patient at an acceptable pressure as discussed above. The cannula 28 is preferably the same as the cannula 28 described above and the aortic occlusion device 2B is introduced through the cannula 28 in the manner described below. The first arm 34 of the cannula 28 has the hemostasis valve 36 for receiving the aortic occlusion device 2B. The second arm 32 is coupled to a valve 90 which determines whether cardioplegic fluid or oxygenated blood is delivered through the lumen 35 in the cannula 28. Valve 92 determines whether oxygenated blood is delivered through the lumen 35 in the cannula 28 or the lumen 88 in the aortic occlusion device 2B. An advantage of the aortic occlusion device 2B and cannula 28 is that bypass support can be provided before inflating the occluding member 4 and can also be maintained after the aortic occlusion device 2B is removed from the cannula 28.

Figure 15:
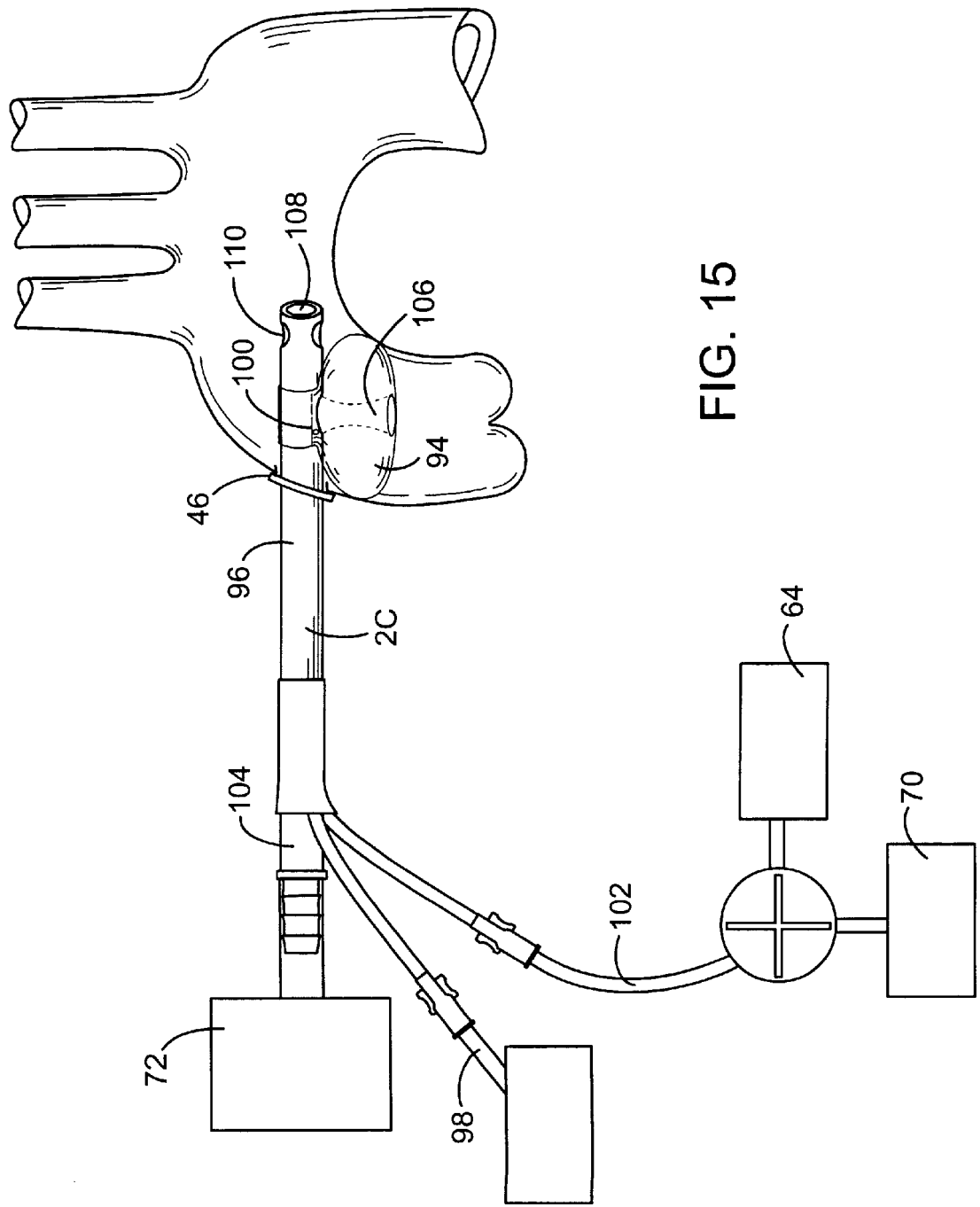
FIG. 15 shows still another aortic occlusion device.

Referring to FIGS. 15, another aortic occlusion device 2C is shown. The aortic occlusion device 2C has a balloon 94 mounted to a side of a shaft 96. The aortic occlusion device 2C has an inflation lumen 98 for inflating the balloon 94 through inflation outlet 100 and a lumen 102 for delivering cardioplegic fluid from the source of cardioplegic fluid 64 and venting the ascending aorta using the vacuum source 70. The aortic occlusion device 2C also has a blood flow lumen 104 for delivering oxygenated blood to the patient from the source of oxygenated blood 72. A fluid path 106 passes through the balloon 94 which is in fluid communication with the lumen 102 so that cardioplegic fluid is delivered through the fluid path 106 in the balloon 94. An advantage of the aortic occlusion device 2C is that the cardioplegic fluid can be delivered toward the aortic valve while oxygenated blood is directed in the direction of normal blood flow in the aortic arch. The distal end of the aortic occlusion device has an open end 108 and side ports 110 through which the oxygenated blood is delivered. The aortic occlusion device 2C also includes the ring 46 which is the same as the ring 46 described above. The aortic occlusion device 2C may be manufactured in any manner such as the manner described above or as a simple extrusion or laminated structure.

Figure 16:
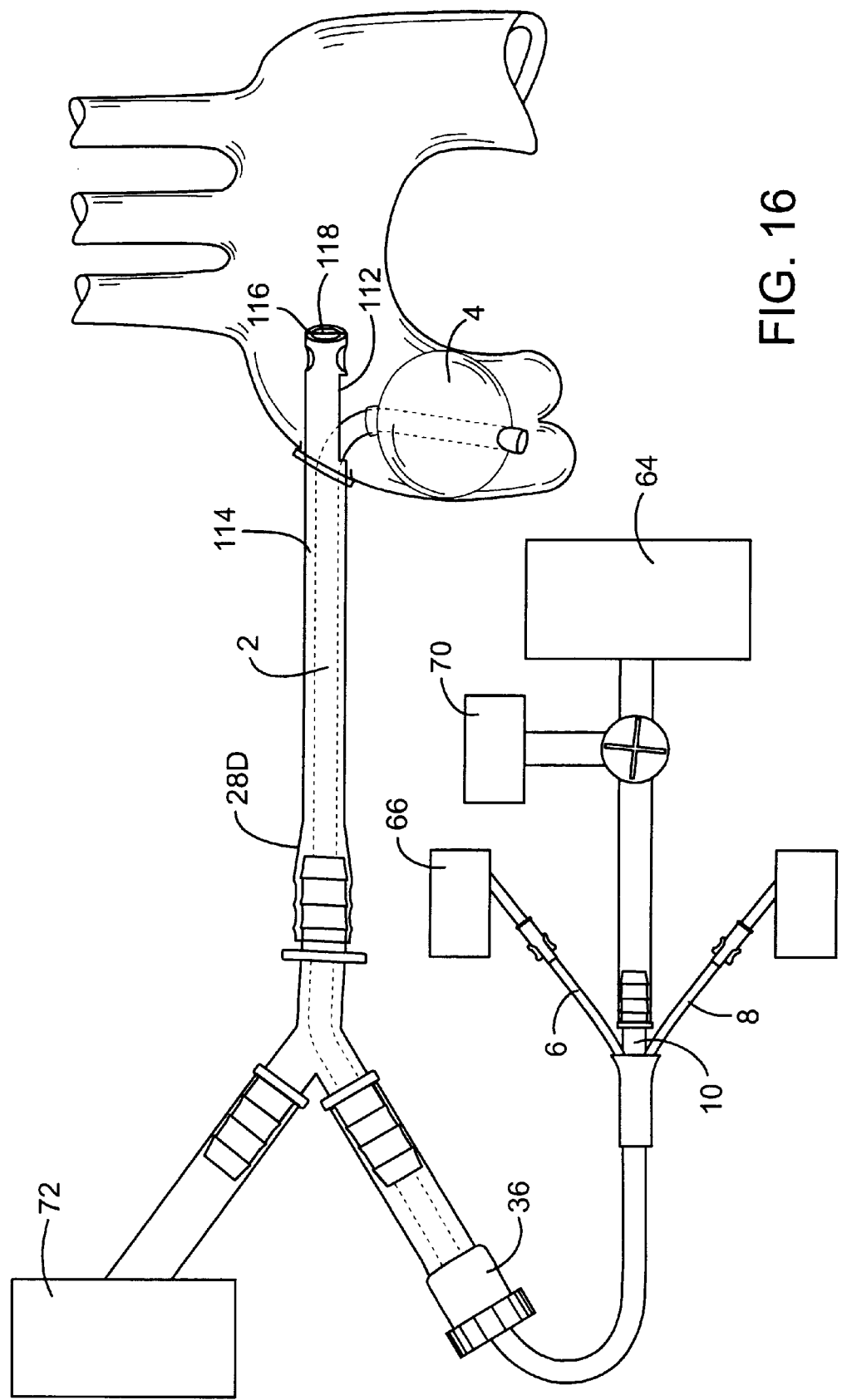
FIG. 16 shows a final aortic occlusion device.

Referring to FIG. 16, the aortic occlusion device 2 is shown passing through a side port 112 of a cannula 28D. The side port 112 facilitates positioning the occluding member 4 in the ascending aorta. The aortic occlusion device 2 is preferably the aortic occlusion device 2 described above.

The aortic occlusion device 2 passes through a lumen 114 in the cannula 28D. The lumen 114 is coupled to the source of oxygenated blood 72 so that the oxygenated blood is delivered through the annular area between the aortic occlusion device 2 and the wall of the lumen 114. The lumen 114 has an open end 116 with a cross-member 118 which prevents the aortic occlusion catheter 2 from passing through the open end 116. An advantage of the side port 112 is that the aortic occlusion device 2 is directed into the ascending aorta while blood passing through the lumen 114 is directed in the direction of normal blood flow in the aorta.

Figure 18:
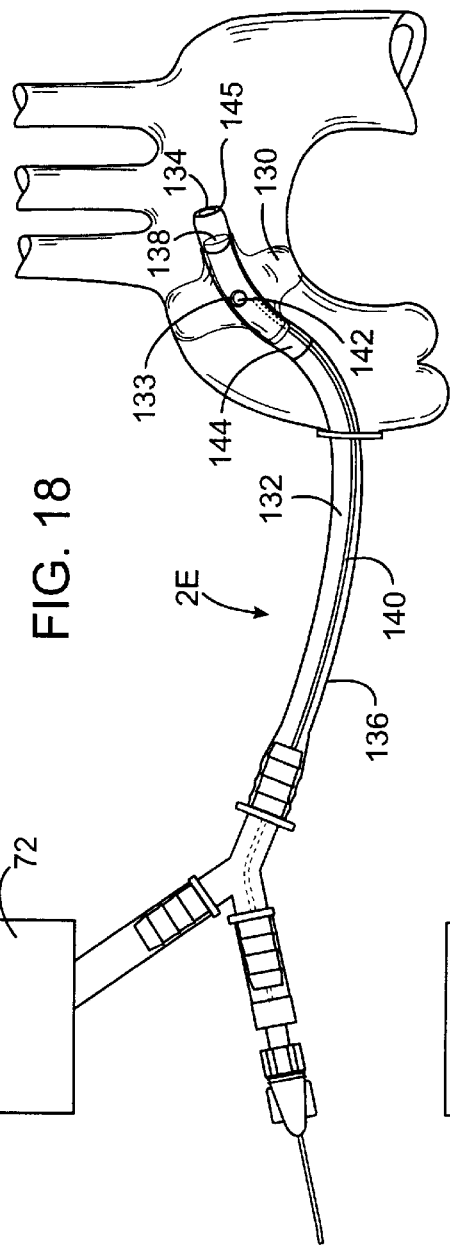
FIG. 18 shows another preferred aortic occlusion device with the balloon occluding the ascending aorta.
Figure 19:
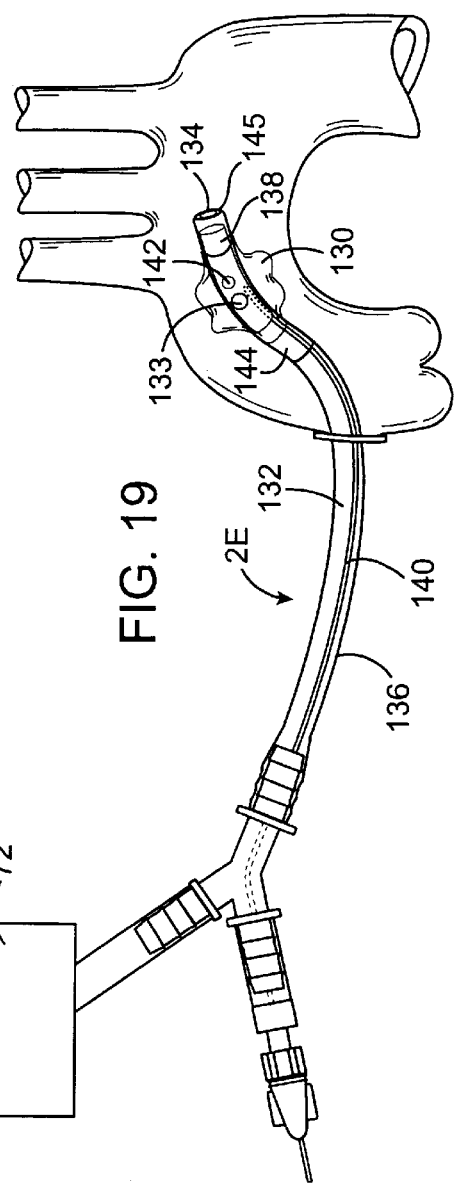
FIG. 19 shows the aortic occlusion device of FIG. 18 with the balloon deflated.

Referring to FIGS. 18 and 19, another aortic occlusion device 2E is shown. The aortic occlusion device 2E is similar to the aortic occlusion device 2A of FIG. 13 in that balloon 130 is inflated with oxygenated blood delivered from the source of oxygenated blood 72. Oxygenated blood is delivered to the patient through a lumen 132 and an open end 134 of the aortic occlusion device 2E. As will be described below, the interior of the balloon 130 is fluidly coupled to the lumen 132 through an inflation hole 133 for inflating the balloon 130 when blood is delivered through the lumen 132.

The aortic occlusion device 2E includes a body 136 having the y-arm connector 30 described above. A sleeve 138 is positioned in the lumen 132 to control inflation and deflation of the balloon 130. Blood passing through the lumen 132 passes through the sleeve 138 so that the sleeve 138 does not interfere with delivery of oxygenated blood to the patient. The sleeve 138 is attached to a rod 140 which is manipulated to move the sleeve 138 between the positions of FIGS. 18 and 19. The sleeve 138 has a hole 142 which is alligned with the inflation hole 133 as shown in FIG. 18 to fluidly couple the interior of the balloon 130 with the lumen 132. When the sleeve 138 is advanced to the position of FIG. 19, the hole 142 is not alligned with the inflation lumen 133 and the sleeve 138 covers the inflation hole 133 so that the interior of the balloon 130 is not fluidly coupled to the lumen 132.

The sleeve 138 permits the surgeon to control inflation and deflation of the balloon 130. After introduction of the aortic occlusion device 2E, bypass support is generally initiated before inflating the balloon 130. This can be accomplished by maintaining the sleeve 138 in the position of FIG. 19 so that the balloon 130 is not inflated by the blood delivered through the lumen 132. When it is desired to inflate the balloon 130 and occlude the ascending aorta, the sleeve 138 is moved to the position of FIG. 18 so that the balloon 130 is inflated with blood. The sleeve 138 also permits the surgeon to maintain full occlusion of the ascending aorta even when blood flow is reduced to a level which would not provide sufficient pressure to inflate the balloon to maintain full occlusion of the aorta. In order to maintain occlusion at low flow rates, the sleeve 138 is moved to the position of FIG. 19 before reducing the blood flow rate so that the balloon 130 will remain inflated when the delivery pressure drops. Finally, the sleeve 138 also permits the surgeon to maintain bypass support with a deflated balloon 130 after the surgical procedure is completed. In order to maintain deflation of the balloon while delivering blood, the blood flow rate is reduced to deflate the balloon 130, the sleeve is moved to the position of FIG. 19 to deflate the balloon, and the blood flow rate is then increased. The sleeve 138 prevents the balloon 130 from inflating when the blood flow rate is increased.

The body 136 may be made in any suitable manner and is preferably manufactured similar to the cannula 28 of FIG. 6. A support tube 144 is attached to the body and the balloon 130 is mounted to the support tube. A soft tip 145 is attached to the distal end of the support tube 144 to provide an atraumatic distal end to prevent injury during introduction of the device 2E. The sleeve 138 may be made of any suitable material and is preferably a urethane tube. The rod 140 may also be made of any suitable material and is preferably urethane coated polyamide. Although it is preferred to provide the sleeve 138 between the interior of the balloon 130 and the lumen 132 any other device may be used such as a valve, balloon or plug.

Figure 17:
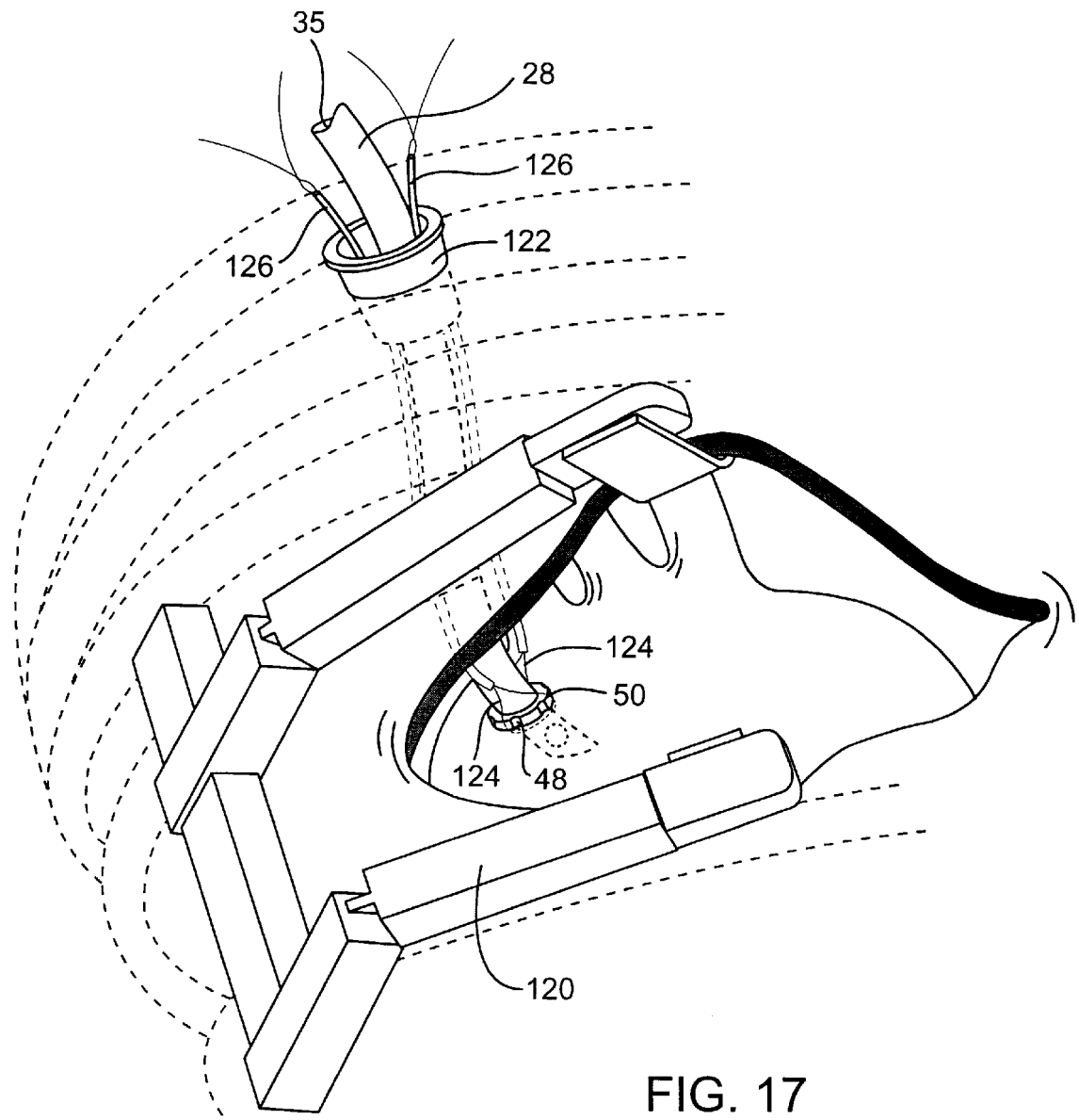
FIG. 17 illustrates a preferred method of introducing the aortic occlusion device.

Use of the cannula and aortic occlusion device 2 is now described in connection with FIGS. 12 and 17. The description below is applicable to all cannulae 28, 28D and aortic occlusion devices 2, 2A, 2B, 2C described herein. Although the method described below is for direct insertion of the cannula 28 and aortic occlusion device 2 into the aortic arch, the cannula 28 and aortic occlusion device 2 may also be introduced through a peripheral artery such as the femoral, subclavian or axillary arteries as described in U.S. Pat. No. 5,484,803.

Before introduction of the cannula, a rib retractor 120 or other device is used to form an opening in an intercostal space such as the $4^{th}$ intercostal space. The opening through the intercostal space is used for access to perform a surgical procedure such as a valve repair or replacement. The opening also provides direct access to the ascending aorta for control of the ascending aorta and to place pursestring sutures in the aorta.

An incision is also created in the $1^{st}$ or $2^{nd}$ intercostal space in which an 11.5 mm trocar 122 is positioned. The cannula 28 is then introduced through the trocar 122 and advanced to the surface of the aorta with the introducer 50 (see FIGS. 10 and 11) positioned in the lumen 35 of the cannula 28 to determine the appropriate orientation of the cannula 28. The distal end of the introducer 50 is then moved into contact with the aorta about 1–2 cm below the origin of the innominate artery to identify the appropriate location for purse-string sutures 124. The surgeon then places two purse-string sutures 124 around the site. The ends of the purse-string sutures 124 are passed through tubes 126 which are used to tension the purse-string sutures 124. The purse-string sutures 124 are then passed through the slots 48 in the ring 46.

The cannula 28 is then advanced into contact with the aorta at the site now surrounded by the purse-string sutures 124. The surgeon then incises the aorta with the incising element 52 of the introducer 50 or with a separate incising instrument. The cannula 28 is then immediately advanced through the incision until the ring 46 engages the aorta. The radiopaque marker 45 may be viewed under fluoroscopy and the cannula 28 manipulated until the beveled tip is directed toward the aortic valve. Alternatively, the tip orientation may be determined by TEE. The purse-string 124 sutures are then tensioned to seal around the cannula 28. The aortic occlusion device 2 is then passed through the hemostasis valve 36 and advanced until the occluding member 4 is positioned in the ascending aorta. Delivery of oxygenated blood, occlusion of the ascending aorta and delivery of cardioplegic fluid is then performed in the manner described in U.S. Pat. No. 5,484,803.

Although the method described above positions the aortic occlusion device through an opening separate from the opening through which the surgeon operates, the cannula and aortic occlusion device 2 may also be introduced through the same opening through which the surgeon operates. The choice of opening location, number and size are a matter of surgical choice depending upon patient anatomy, the medical procedure being performed, surgeon preference and the particular embodiment of the invention being used. Furthermore, the devices described herein may have application in other parts of the heart and in other parts of the body. Thus, the description of the specific procedure described above is merely an example and other surgical methods may be used with the devices and methods of the present invention.

What is claimed is:

1. A method of occluding a patient's ascending aorta and delivering oxygenated blood to the patient, comprising the steps of:

providing an aortic occlusion device having a blood delivery lumen and an occluding member, the occluding member having an interior in fluid communication with the blood delivery lumen, the occluding member being a balloon having at least one opening therein, wherein blood in the balloon passes directly through the at least one opening in the balloon;

inserting the aortic occlusion device into a patient's ascending aorta;

coupling the blood delivery lumen to a source of oxygenated blood;

delivering oxygenated blood through the blood delivery lumen from the source of oxygenated blood so that the oxygenated blood inflates the occluding member and occludes the ascending aorta, the oxygenated blood being delivered directly through the at least one opening in the balloon and also being delivered to the patient to maintain circulation of oxygenated blood in the patient when the ascending aorta is occluded.

2. The method of claim 1, further comprising the step of:

delivering cardioplegic fluid to the patient's ascending aorta to arrest the patient's heart;

the providing step being carried out with the aortic occlusion device having a cardioplege lumen, the cardioplege lumen being coupled to a source of cardioplegic fluid.

3. The method of claim 1, further comprising:

a device disposed between the lumen and an interior of the balloon, the device being movable between a first position and a second position, the interior of the balloon being fluidly coupled to the lumen when in the device is in the first position and the balloon being fluidly isolated from the lumen when the device is in the second position.

4. A method of occluding a patient's ascending aorta and delivering oxygenated blood to the patient, comprising the steps of:

providing a cannula and an aortic occlusion device, the cannula having a lumen, the aortic occlusion device having a blood flow lumen and an occluding member, the blood flow lumen having an outlet, the occluding member being movable between a collapsed position and an expanded position;

inserting the cannula into a patient's ascending aorta;

passing the aortic occlusion device through the lumen of the cannula so that the occluding member is positioned in the ascending aorta;

coupling the blood flow lumen of the aortic occlusion device to a source of oxygenated blood;

infusing oxygenated blood into the patient through the blood flow lumen from the source of oxygenated blood.

5. The method of claim 4, further comprising the step of:

infusing cardioplegic fluid into the ascending aorta through the cannula.

6. The method of claim 5, wherein:

the infusing step is carried out by passing the cardioplegic fluid through the lumen in the cannula.

7. The method of claim 4, further comprising the step of:

coupling the lumen of the cannula to the source of oxygenated blood;

removing the aortic occlusion catheter from the lumen of the cannula; and infusing oxygenated blood into the patient through the lumen of the cannula.

8. A system for occluding a patient's ascending aorta and delivering oxygenated blood to the patient, comprising:

a cannula having a lumen;

an aortic occlusion device having a blood delivery lumen and an occluding member, the occluding member having an interior in fluid communication with the blood delivery lumen, the aortic occlusion device passing through the lumen, wherein the occluding member is a balloon having at least one opening therethrough which blood within the balloon passes directly through; and a source of oxygenated blood coupled to the blood delivery lumen.

9. The system of claim 8, further comprising:

a source of cardioplegic fluid fluidly coupled to the lumen of the cannula.

10. A system of occluding a patient's ascending aorta and delivering oxygenated blood to the patient, comprising the steps of:

a cannula having a lumen;

an aortic occlusion device having a blood flow lumen and an occluding member, the blood flow lumen having an outlet, the occluding member being movable between a collapsed position and an expanded position, the aortic occlusion device passing through the lumen of the cannula;

a source of oxygenated blood coupled to the blood flow lumen of the aortic occlusion device; and a source of cardioplegic fluid coupled to the lumen of the cannula.

11. The system of claim 10, wherein:

the lumen of the cannula is also fluidly coupled to the source of oxygenated blood via a valve.

* * * * *